(12) United States Patent
Liu et al.

(10) Patent No.: US 10,941,453 B1
(45) Date of Patent: Mar. 9, 2021

(54) HIGH THROUGHPUT DETECTION OF PATHOGEN RNA IN CLINICAL SPECIMENS

(71) Applicant: Paragon Genomics, Inc., Hayward, CA (US)

(72) Inventors: Zhitong Liu, Foster City, CA (US); Chenyu Li, Hayward, CA (US); David Debruyne, Foster City, CA (US); Guoying Liu, San Ramon, CA (US)

(73) Assignee: Paragon Genomics, Inc., Hayward, CA (US)

( * ) Notice: Subject to any disclaimer, the term of this patent is extended or adjusted under 35 U.S.C. 154(b) by 0 days.

(21) Appl. No.: 16/879,742

(22) Filed: May 20, 2020

(51) Int. Cl.
*C12Q 1/68* (2018.01)
*C12Q 1/70* (2006.01)
*C12Q 1/6874* (2018.01)
*C12N 15/10* (2006.01)

(52) U.S. Cl.
CPC .......... *C12Q 1/701* (2013.01); *C12N 15/1013* (2013.01); *C12N 15/1096* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,168,038 A | 12/1992 | Tecott et al. | |
| 5,210,015 A | 5/1993 | Gelfand et al. | |
| 5,399,491 A | 3/1995 | Kacian et al. | |
| 5,539,082 A | 7/1996 | Nielsen et al. | |
| 5,750,341 A | 5/1998 | Macevicz | |
| 5,854,033 A | 12/1998 | Lizardi | |
| 5,925,517 A | 7/1999 | Tyagi et al. | |
| 6,174,670 B1 | 1/2001 | Wittwer et al. | |
| 6,670,461 B1 | 12/2003 | Wengel et al. | |

(Continued)

FOREIGN PATENT DOCUMENTS

| | | |
|---|---|---|
| CN | 101575597 A | 11/2009 |
| JP | H04262799 A | 9/1992 |

(Continued)

OTHER PUBLICATIONS

Aboul-Maaty et al.; Extraction of high-quality genomic DNA from different plant orders applying a modified CTAB-based method; Bulletin of the National Research Centre; 43(1); 10 pages, doi 10.1186/s42269-019-0066-1; Dec. 2019.

(Continued)

*Primary Examiner* — Aaron A Priest
(74) *Attorney, Agent, or Firm* — Shay Glenn LLP

(57) ABSTRACT

Laboratory-based high throughput methods and compositions (e.g., kits) for the detection of pathogen mRNA, including in particular, for the detection of SARS-CoV-2 RNA from up to 85,000 samples in one Illumina NovaSeq sequencing run. These methods may include barcoding cDNA, indexing pools of libraries and intensive use of automatic liquid handling, providing a ready-to-sequence library mix. These methods and compositions may allow a very inexpensive per sample cost and an assay that may be performed in about one day or less.

24 Claims, 4 Drawing Sheets

(56) References Cited

U.S. PATENT DOCUMENTS

| | | | |
|---|---|---|---|
| 8,586,310 B2 | 11/2013 | Mitra et al. | |
| 8,673,560 B2 | 3/2014 | Leamon et al. | |
| 8,685,678 B2 | 4/2014 | Casbon et al. | |
| 9,464,318 B2 | 10/2016 | Liu | |
| 9,556,427 B2 | 1/2017 | Ji | |
| 9,752,188 B2 | 9/2017 | Schmitt et al. | |
| 10,100,358 B2* | 10/2018 | Liu | C12Q 1/686 |
| 10,421,993 B2 | 9/2019 | Liu et al. | |
| 2004/0185484 A1 | 9/2004 | Costa et al. | |
| 2008/0014634 A1 | 1/2008 | Greener et al. | |
| 2009/0123913 A1 | 5/2009 | Barany et al. | |
| 2009/0203085 A1 | 8/2009 | Kum | |
| 2013/0261027 A1 | 10/2013 | Li et al. | |
| 2014/0227705 A1 | 8/2014 | Vogelstein et al. | |
| 2014/0322716 A1* | 10/2014 | Robins | C12Q 1/6846 435/6.12 |
| 2014/0329945 A1 | 11/2014 | Spier et al. | |
| 2014/0357500 A1* | 12/2014 | Vigneault | C07K 16/00 506/4 |
| 2014/0378317 A1 | 12/2014 | Fu et al. | |
| 2016/0024493 A1* | 1/2016 | Robins | C12N 15/1093 506/2 |
| 2016/0122753 A1* | 5/2016 | Mikkelsen | C12Q 2525/101 506/4 |
| 2016/0312276 A1* | 10/2016 | Fu | C12Q 1/6855 |
| 2017/0114406 A1* | 4/2017 | Hansen | C12Q 1/6876 |
| 2018/0010176 A1* | 1/2018 | Patel | C12Q 1/6806 |
| 2018/0030515 A1* | 2/2018 | Regev | C12Q 1/6809 |
| 2018/0163201 A1* | 6/2018 | Larson | C12Q 1/6855 |
| 2019/0010489 A1* | 1/2019 | Chang | C40B 40/08 |
| 2020/0109437 A1* | 4/2020 | Chang | C12Q 1/6806 |
| 2020/0156071 A1* | 5/2020 | Hansen | C12M 23/16 |
| 2020/0208143 A1 | 7/2020 | Liu et al. | |

FOREIGN PATENT DOCUMENTS

| | | |
|---|---|---|
| WO | WO2005/095605 A1 | 10/2005 |
| WO | WO2006/127423 A2 | 11/2006 |
| WO | WO2006/138444 A2 | 12/2006 |
| WO | WO2008/061193 A2 | 5/2008 |
| WO | WO2012/149438 A1 | 11/2012 |
| WO | WO20115/063154 A1 | 5/2015 |
| WO | WO2016/040901 A1 | 3/2016 |

OTHER PUBLICATIONS

Allawi et al.; Thermodynamics and NMR of internal GO T mismatches in DNA; Biochemistry; 36(340); pp. 10581-10594; Aug. 1997.

Anderson et al.; Protocol: a versatile, inexpensive, high-throughput plant genomic DNA extraction method suitable for genotyping-by-sequencing; Plant Methods; 14(1); 10 pages, doi.org/10.1186/s13007-018-0336-1; Dec. 2018.

Babon et al; The use of resolvases T4 endonuclease VII and T7 endonuclease I in mutation detection; in Methods in Molecular Biology: vol. 152: DNA Repair Protocols: Prokaryotic systems; Edited by P. Vaughan; © Humana Press Inc.; Totowa, NJ; pp. 187-199; Jul. 2000.

Bernard et al.; Color multiplexing hybridization probes using the apolipoprotein E locus as a model system for genotyping; Anal. Biochem.; 273(2); pp. 221-228; Sep. 10, 1999.

Casbon et al.; A method for counting PCR template molecules with application to next-generation sequencing; Nucleic Acids Res.; 39(12); 8 pages; e81.doi: 10.1093/nar/gkr217; Jul. 2011.

Chen et al.; Generation and analysis of a barcode-tagged insertion mutant library in the fission yeast schizusaccharomyces pombe; BMC Genomics; 13(1); 18 pages; retrieved from the internet (http://www.biomedcentral.com/1471-2164/13/161; Dec. 2012.

Crooke et al.; Section review biologicals and immunologicals: Progress in the development and patenting of antisense drug discovery technology; Expert Opinion on Therapeutic Patents; 6(9); pp. 855-870; Sep. 1, 1996.

Fu et al.; Counting individual DNA molecules by the stochastic attachment of diverse labels; Proc. Natl. Acad. Sci. USA; 108(22); pp. 9026-9031; May 31, 2011.

Fuhrmann et al.; Removal of mismatched bases from synthetic genes by enzymatic mismatch cleavage; Nucleic Acids Research; 33(6); 8 pages; doi:10.1093/nar/gni058; Jan. 2005.

Gregory et al.; Targeted single molecule mutation detection with massively parallel sequencing; Nucleic Acids Res.; 44(3); 11 pages; e22. doi:10.1093/nar/gkv915; Feb. 18, 2016.

Hill-Ambroz et al.; Modified rapid DNA extraction protocol for high throughput microsatellite analysis in wheat; Crop Science; 42(6); pp. 2088-2091; 4 pages, doi:10.2135/cropsci2002.2088; Nov. 2002.

Hoffmann et al.; DNA bar coding and pyroseguencing to identify rare HIV drug resistance mutations; Nucleic Acids Res.; 35(13); 8pages; e91, doi.10.1093/nar/gkm435; ; Jun. 18, 2007.

Kanehisa ; Use of statistical criteria for screening potential homologies in nucleic acid sequences; Nucleic Acids Res.; 12(1 prt 1); pp. 203-213; Jan. 11, 1984.

Kasajima; Successful tips of DNA extraction and PCR of plants for beginners; Trends in Research; 1(3): 1-2, 5 pages doi:10.15761/TR. 1000115: Sep. 2018.

Kivioja et al.; Counting absolute numbers of molecules using unique molecular identifiers; Nat. Methods; 9(1); pp. 72-74; (Author Manuscript); Nov. 20, 2011.

Leone et al; Molecular beacon probes combined with amplification by NASBA enable homogeneous, real-time detection of RNA; Nucleic Acids Res.; 26(9); pp. 2150-2155; May 1, 1998.

Li et al.; A universal method for direct PCR amplification of plant tissues; Analytical Methods; 9(11); pp. 1800-1805; 6 pages, doi: 10.1039/C6AY03156K; (year of pub. sufficiently earlier than effective US filing date and any foreign priority date) 2017.

Lowell et al.; Heteroduplex resolution using T7 endonuclease I in microbial community analyses; Bio Techniques; 28(4); pp. 676-681; Apr. 2000.

Mackay et al.; Real-time PCR in virology; Nucleic Acids Research; 30(6); pp. 1292-1305; Mar. 15, 2002.

Mardis; The impact of next-generation sequencing technology on genetics; Treand in Genetics; 24(3); pp. 133-141; Mar. 1, 2008.

McDonough et al.; Use of FFPE-derived DNA in next generation sequencing: DNA extraction methods; Plos one; 14(4); 15 pages; doi: 10.1371/journal.pone.0211400; Apr. 2019.

Mesmaeker et al.; Backbone modifications in oligonucleotides and peptide nucleic acid systems; Current Opinion in Structural Biology; 5(3); pp. 343-355; Jun. 1995.

Newman et al.; Integrated digital error suppression for imptoved detection of circulating tumor DNA; Nature Biotechnology; 34(5); pp. 547-555, doi:10.1038/nbt.3520; (Author Manuscript); May 2016.

Phallen et al.; Direct detection of early-stage cancers using circulating tumor DNA; Sci. Transl. Med.; 9(403); pii: eaan2415. dol: 10.1126/scritranslmed.aan2415; Aug. 16, 2017.

Rana et al.; Optimized nuclear pellet method for extracting next-generation sequencing quality genomic DNA from fresh leaf tissue; Methods and protocols. 2(2):54; 11 pages, doi: 10.3390/mps2020054; ; Jun. 2019.

Qiu et al.; Evaluation of PCR-generated chimeras, mutations, and heteroduplexes with 16S rRNA gene-based cloning. Applied and Environmental Microbiology. 67(2): pp. 880-887; Feb. 1, 2001.

Schmitt et al.; Detection of ultra-rare mutations by next-generation sequencing; Proc. Natl. Acad. Sci. USA; 109(36); pp. 14508-14513; Sep. 4, 2012.

Shendure et al.; Next-generation DNA sequencing; Nature Biotechnology; 26 (10); pp. 1135-1145; Oct. 2008.

Stahlberg et al.; Simple, multiplexed, PCR-based barcoding of DNA enables sensitive mutation detection in liquid biopsies using sequencing; Nucleic Acids Res.; 44(11): pp. 1-7; e105. doi: 10.1093/nar/gkw224; Jun. 20, 2016.

Stoler et al.; Streamlined analysis of duplex sequencing data with du novo; Genome Biology; 17(1); 10 pages; DOI 10.1186/s13059-016-1039-4; Dec. 2016.

Su et al.; Next-generation sequencing and its applications in molecular diagnostics; Expert Rev. Mol. Diagn.; 11(3); pp. 333-343; Apr. 2011.

(56) References Cited

OTHER PUBLICATIONS

Takishita et al.; Genetic diversity of microbial eukaryotes in anoxic sediment of the saline meromictic lake namako-ike (japan): on the detection of anaerobic or anoxic-tolerant lineages of eukaryotes; Protist; 158(1); pp. 51-64; Jan. 2007.

Tan et al:; DNA, RNA, and protein extraction: the past and the present: Journal of Biomedicine and Biotechnology; Hindawi Publishing Corporation; 10 pages; doi:10.1155/2009/574398; Nov. 2009.

Uhlman et al.; Antisense oligonucleotides: a new therapeutic principle; Chemical Reviews; 90(4); pp. 543-584; Jun. 1, 1990.

Von Post et al.; A high-throughput DNA extraction method for barley seed; Euphytica; 130(2); pp. 255-260; 6 pages, doi 10.1023/A:1022863006134; Mar. 2003.

Wang et al.; A rapid and cheap protocol for preparation of PCR templates in peanut: Electronic Journal of Biotechnology; 12(2); pp. 9-10; 7 pages, doi 10.2225/vol12-issue2-fulltext-11; Apr. 2009.

Wang et al.; A simple method of preparing plant samples for PCR; Nucleic Acids Research; 21(17); pp. 4153-4154; Aug. 1993.

Wang et al.; Targeted sequencing of both DNA strands barcoded and captured individually by RNA probes to identify genome-wide intra-rare mutations; Scientific Reports; 7(1); 14 pages; 3356 DOI:10.1038/s41598-017-03448-8; Jun. 13, 2017.

Werner et al.; Direct amplification and NaOH extraction: two rapid and simple methods for preparing bryophyte DNA for polymerase chain reaction (PCR); Journal of Bryology; 24(2): pp. 127-131; 5 pages, doi: 10.1179/037366802125000980; Jun. 2002.

Young et al.; Efficient isolation of genes by using antibody probes; Proc. Natl. Acad, Sci.USA; 80(5); pp. 1194-1198; Mar. 1983.

Zhang et al.; The impact of next-generation sequencing on genornics; J. Genet. Genomics; 38(3); pp. 95-109; (Author Manuscript) Mar. 20, 2011.

Zhang et al.; Elimination of primer-dimer effect in SYBR green I real-time RT-PCR using 4-step program. Chinese Journal of Biochemistry and Molecular Biology; 2004; 20(3); pp. 387-392; (Machine Translated English Abstract); Dec. 31, 2003.

Lin et al.; A convenient method to remove primer dimer in polymerase chain reaction; Journal of Xinxiang Medical College; 29(6); pp. 617-418, 421; (Machine Translated English Abstract); Jun. 5, 2012.

Liu et al.; U.S. Appl. No. 16/716,487 entitled Methods and systems to amplify short RNA targets,: filed Dec. 16, 2019.

Liu et al.; U.S. Appl. No. 16/741,272 entitled "Methods and compositions for preparation of crude lysate of nucleic acids," filed Jan. 13, 2020.

Juvonen el al.; Amplification Facilitators and Pre-Processing Methods for PCR Detection of Strictly Anaerobic Beer-Spoilage Bacteria of the Class Clostridia in Brewery Samples; Journal of the Institute of Brewing and Distilling; 115(3); pp. 167-176; Aug. 1, 2009.

\* cited by examiner

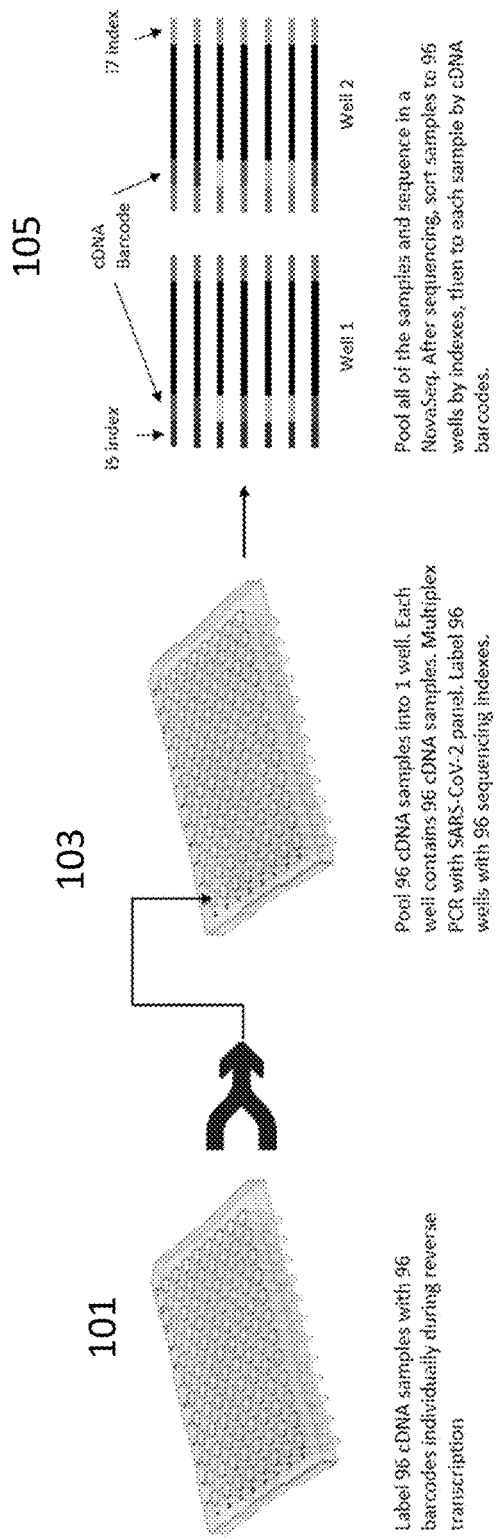
FIG. 1
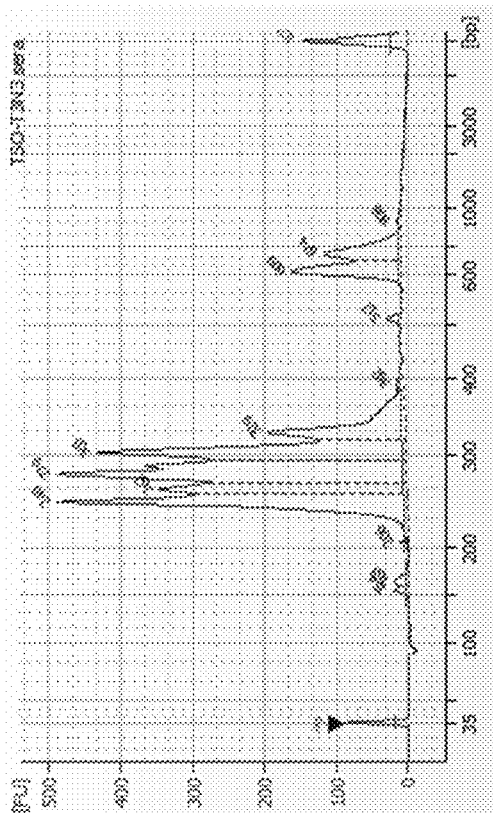
FIG. 3
FIG. 2

HIGH THROUGHPUT DETECTION OF PATHOGEN RNA IN CLINICAL SPECIMENS

CROSS REFERENCE TO RELATED APPLICATIONS

None.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

High-throughput sequencing, or next-generation sequencing (NGS), is being applied to generate data across many disciplines. NGS instruments are becoming less expensive, faster, and smaller, and therefore are being adopted in an increasing number of laboratories, including clinical laboratories. Thus far, clinical use of NGS has been mostly focused on the human genome, for purposes such as characterizing the molecular basis of cancer or for diagnosing and understanding the basis of rare genetic disorders. There are, however, an increasing number of examples whereby NGS is employed to discover novel pathogens, and these cases provide precedent for the use of NGS in microbial diagnostics.

NGS has many advantages over traditional microbial diagnostic methods, such as unbiased rather than pathogen-specific protocols, ability to detect fastidious or non-culturable organisms, and ability to detect co-infections. Despite these advantages, NGS has not been successfully implemented for routine clinical pathogen diagnosis. Described herein are methods and compositions (e.g., kits) that may incorporate next generation sequencing for pathogen detection.

SUMMARY OF THE DISCLOSURE

Described herein are high throughput methods of diagnosing a pathogen by detecting pathogen RNA, using a multiplex primer extension reaction. In particular, these methods may be used for detecting and/or diagnosing SARS-Cov-2 (COVID-19). For example, a method may include: purifying pathogen RNA from a plurality of clinical specimens; breaking the RNA into small fragments; converting RNA into n cDNA preparations by reverse transcription, in one or more multi-well plates, and labeling each cDNA preparation with a barcode by a template switching reaction that takes place simultaneously; pooling each of the n cDNA preparations into one vessel, purifying the cDNA, and loading the purified cDNA mix into a plurality of m wells of one or more new multi-well plates; amplifying a plurality of targets of the pathogen in each of the m wells by multiplex PCR with a plurality of target-specific primers to form m libraries, followed by indexing PCR where each of the m wells is labeled with one specific pair of sequencing indexes; mixing all of the m libraries made in the m multi-well plates into one or more pools, purifying and sequencing the one or more pools in a next generation sequencer; and sorting the indexes and barcodes to identify each sample.

In general, the pathogen RNA may be any type or amount of pathogen RNA. For example pathogen RNA may be total RNA, mRNA, fragmented total RNA, or fragmented mRNA. The pathogen RNA may be taken from any sample. For example pathogen RNA may be taken from (e.g., purified from) one or more of: nasopharyngeal swabs, blood, plasma, body fluid, feces, Formalin-fixed, and Paraffin-embedded (FFPE) tissue samples (FFPE RNA).

As used herein "purifying" pathogen RNA is not limited to purifying isolated pathogen RNA, but may including purifying pathogen and non-pathogen RNA.

In some variations, pathogen RNA may be the total RNA containing RNA of a sample that may contain the pathogen, including, e.g., RNA of SARS-CoV-2 virus, included from one or more of: nasopharyngeal swabs, blood, plasma, body fluid, feces, Formalin-fixed, and Paraffin-embedded (FFPE) tissue samples (FFPE RNA). Purifying may mean separating completely or partially from non-RNA material (e.g. protein, etc.).

The template switching reaction may include, a template switching oligo. Examples of template switching may be found, for example, in U.S. patent application Ser. No. 16/716,487, filed Dec. 16, 2019("METHODS AND SYSTEMS TO AMPLIFY SHORT RNA TARGETS") and herein incorporated by reference in its entirety. The template switching oligo may contain a barcode or a unique molecular index comprising 3-8 random nucleotides.

In any of these examples, the cDNA may be synthesized during the conversion of the RNA into n cDNA preparations by using between about 0.2-2 uM of oligo(dT), between about 1-10 uM of hexamer primer, between about 1-10 uM of template switching oligo and between about 10-200 units of reverse transcriptase at about 42° C. for about 90 minutes.

The reverse transcription reaction may be further treated by using an exonuclease, multiple exonucleases, or a combination of exonucleases and nucleases, selected from the group comprising: S1 nuclease, P1 nuclease, mung bean nuclease, lambda exonuclease, exonuclease I, exonuclease VII, exonuclease T, RecJ, RecJf.

The plurality of target-specific primers may include a target-specific region that is complimentary to a plurality of target RNA (e.g., pathogen RNA). For example, the plurality of target-specific primers may include a target-specific region that is complimentary to a plurality of target RNA. The plurality of target-specific primers may include either forward primers or reverse primers. In some variations, the plurality of target-specific primers comprises both forward primers and reverse primers. For example, each primer of the plurality of primers may include a target-specific region that is from 8-50 nucleotides. The plurality of target-specific primers may comprise between 7 target-specific primers and 1,000,000 target-specific primers. Each primer of the plurality of target-specific primers may include a target-specific region comprising unmodified oligonucleotides. In some variations, each primer of the plurality of target-specific primers includes a target-specific region comprising modified oligonucleotides with chemical modifications of nucleotides. Each primer of the plurality of target-specific primers may comprise a region of nucleotide sequence used for further amplification and for high-throughput sequencing.

Any of these methods may also include purifying the cDNA using magnetic beads or a DNA purification column. The multiplex primer extension reaction may be a multiplex polymerase chain reaction. For example, the method may include amplifying the products of the multiplex polymerase chain reaction with a pair of primers that contain sequencing indexes, or unique dual indexes. The multiplex primer extension reaction may be further treated by using an exonuclease, multiple exonucleases, or a combination of exonucleases and nucleases, selected from the group comprising: S1 nuclease, P1 nuclease, mung bean nuclease, lambda exonuclease, exonuclease I, exonuclease VII, exonuclease T, RecJ, RecJf.

Any of these methods may include analyzing the amplification products by high-throughput sequencing.

For example, described herein are high throughput methods of diagnosing SARS-CoV-2 using a multiplex primer extension reaction. The method may include: purifying RNA including SARS-CoV-2 RNA from a plurality of clinical specimens; breaking the RNA into small fragments; converting RNA into n cDNA preparations by reverse transcription, in one or more multi-well plates, and labeling each cDNA preparation with a barcode by a template switching reaction that takes place simultaneously; pooling each of the n cDNA preparations into one vessel to form a cDNA mix, purifying the cDNA, and loading the purified cDNA mix into a plurality of m wells of one or more new multi-well plates; amplifying a plurality of targets of the pathogen in each of the m wells by multiplex PCR with a plurality of SARS-CoV-2 specific primers to form m libraries, followed by indexing PCR where each of the m wells is labeled with one specific pair of sequencing indexes; mixing all of the m libraries made in the m multi-well plates into one or more pools, purifying and sequencing the one or more pools in a next generation sequencer; and sorting the indexes and barcodes to identify each sample. The plurality of SARS-CoV-2 specific primers may span greater than 50% of a genome of SARS-Cov-2(e.g., 50% or more, 55% or more, 60% or more, 65% or more, 70% or more, 75% or more, 80% or more, 85% or more, 90% or more, 95% or more, etc.). For example, the plurality of SARS-CoV-2 specific primers may span greater than 80% of a genome of SARS-Cov-2.

Also described herein are kits for performing any of these methods, including kids containing any of these solutions (buffers, enzymes, etc.), primers, etc.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 1 illustrates one example of a strategy of high throughput detection of SARS-CoV-2 RNA. In this example, by applying a layer of barcodes on cDNA, and a layer of indexes on the libraries, 96 by 96 samples can be processed in one 96- well plate and sequenced all together in a NovaSeq flow cell.

FIG. 2 illustrates one example of template switching used to barcode cDNA. cDNA is synthesized with random hexamers as primers. Three Cs are synthesized at the 3' end of a nascent cDNA by the template-independent activity of the reverse transcriptase. An oligo (Adapter-BC-GGG) is used to hybridize onto CCC, and "trick" the reverse transcriptase into extending the cDNA synthesis. The resulting cDNA is labeled with a barcode and an adapter. Template switching of the random hexamer on the right is blocked by the random hexamer on the left, showing that the fragmentation of RNA is required. The cDNA is amplified with a target-specific primer and a universal primer (larger arrows).

FIG. 3 illustrates the performance of template switching in one example of a CleanPlex method as described herein.

The cDNA barcoded with template switching was used in a multiplex PCR reaction to amplify the targets that contain fusion mutations, followed by sequencing. A panel of 61 primers and a universal primer were used in the multiplex PCR. A reference RNA mix that contains known fusion mutations was used as the template. No obvious amounts of primer-dimers were found in the library QC shown in FIG. 3. After sequencing, it was found that 93.6% of the recovered reads were on-target, while rRNA and non-specific products occupied the remaining 6.4% reads.

Figure 4:
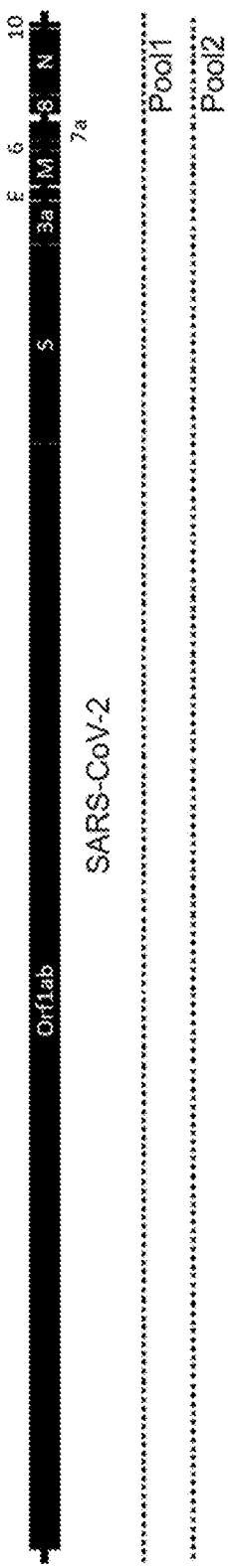

FIG. 4 illustrates the design of one example of a SARS-CoV-2 multiplex PCR primer pool. Two overlapping pools of multiplex PCR primers, shown in FIG. 4 below the genome of SARS-CoV-2, were designed based on over 1,100 full SARS-CoV-2 genomes from GISAID database. Together with additional degenerated primers, this panel covers 99.69% of SARS-CoV-2 genome with the potential to amplify both known and emerging mutants. Pool 1, containing 172 pairs of primers, covers 56.9% of the viral genome. Pool 2 contains 171 pairs of primers and covers 56.4% of the genome and is used in the detection.

Figure 5:
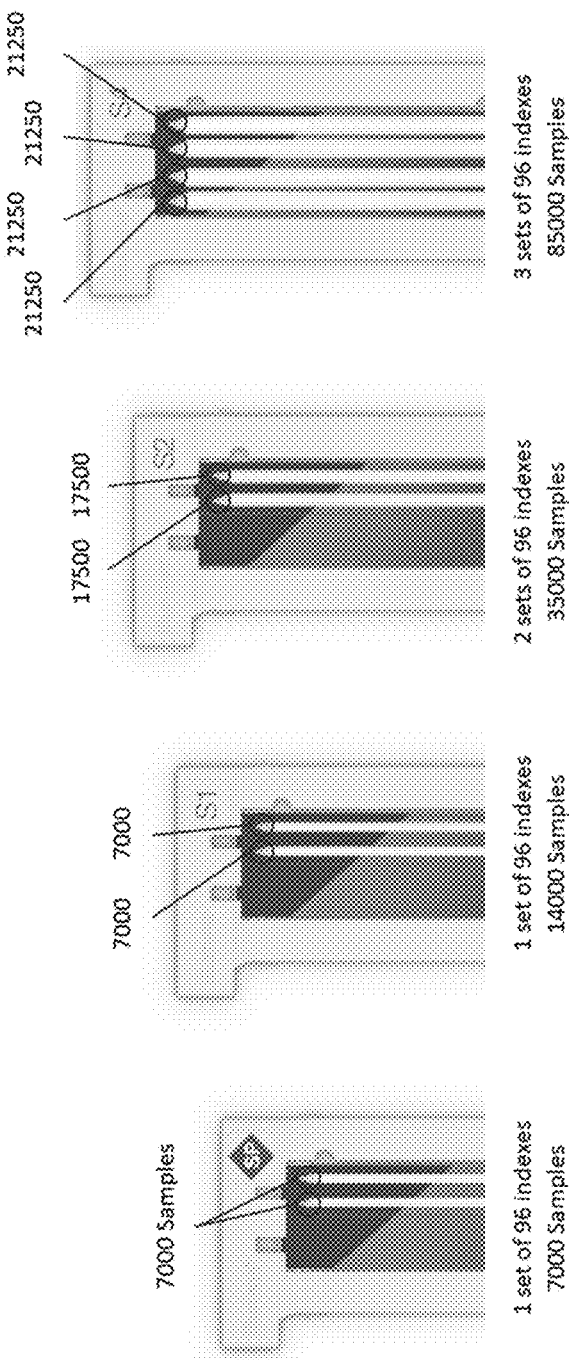

FIG. 5 shows a number of samples that can be sequenced in each of the NovaSeq flow cells, shown on the top of the flow cells. The same set of indexes can be repeatedly used in the lanes of the flow cells since the lanes are separated physically.

Figure 6:
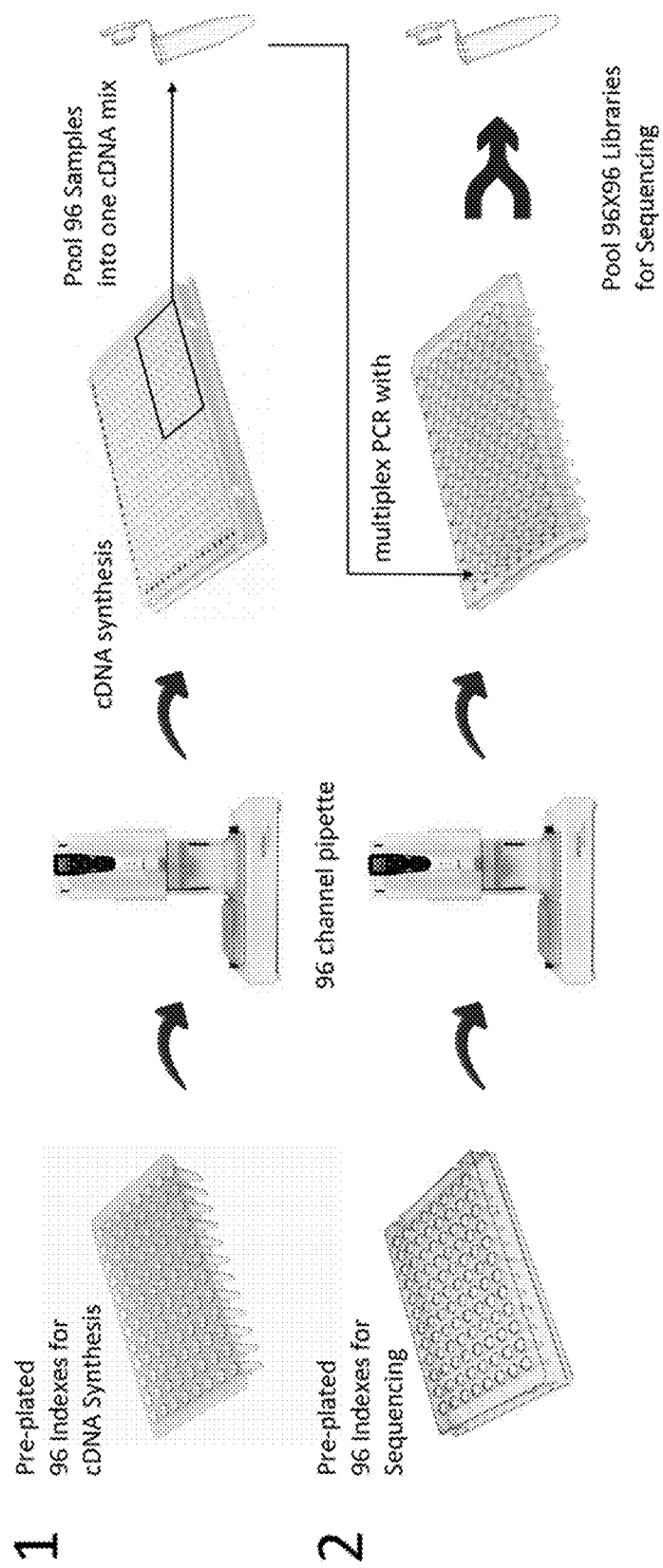

FIG. 6 illustrates cDNA synthesis and barcoding carried out in 384-well plates, where one set of 96 barcodes is repeatedly used to label cDNAs. Pre-plated barcodes and indexes may be transferred by a 96-channel pipette to minimize cross-contamination.

Figure 7:
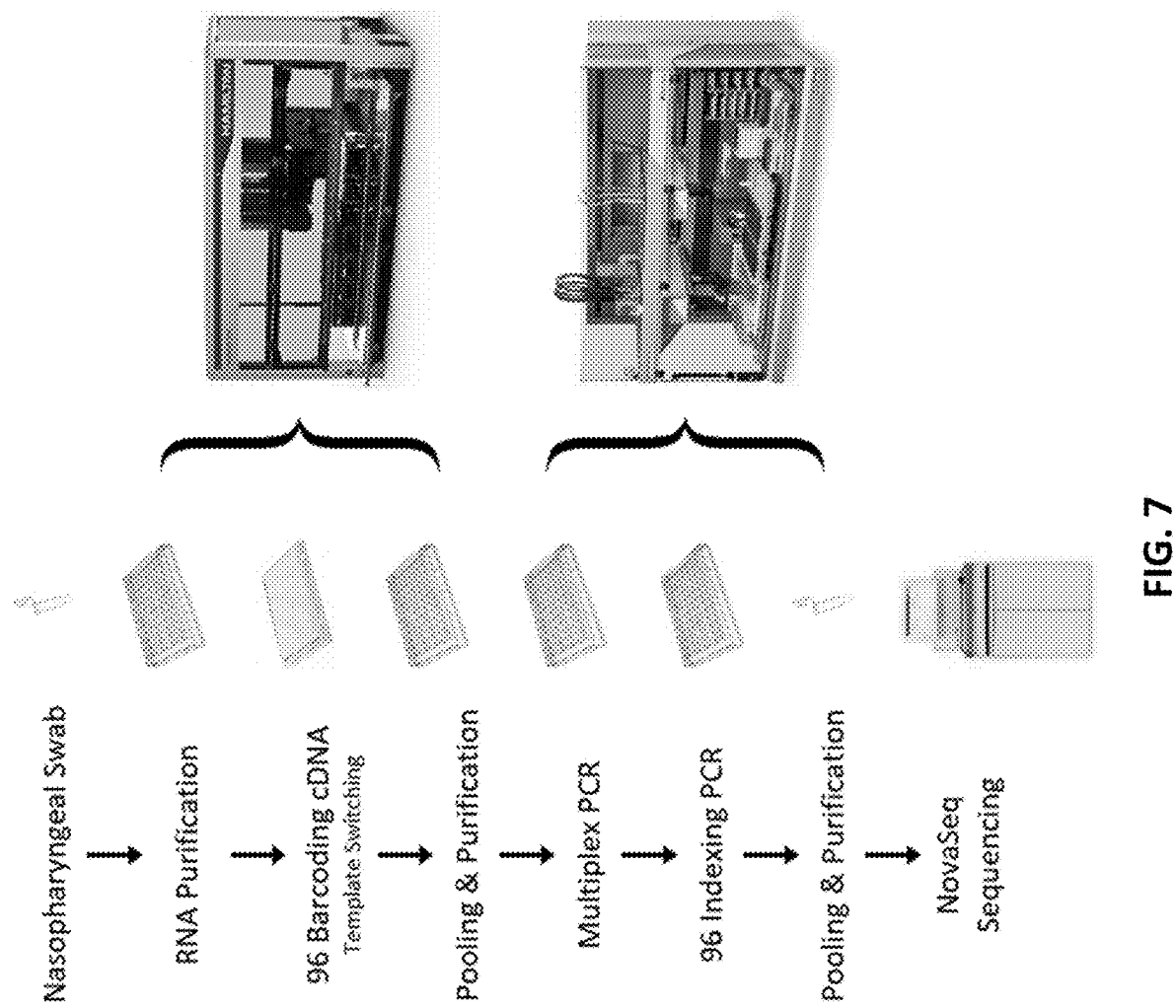

FIG. 7 illustrates one example of automatic liquid handling used for RNA purification, assembling the reactions of reverse transcription, the multiplex PCR, indexing PCR, pooling and purification, as described herein. Manual loading and unloading of the above reactions may otherwise be used. A 384-head (shown in this example with a Hamilton Microlab Star) is used for reverse transcription and pooling to prevent cross-contamination, and a 96-head (Tecan EVO 150) is used in the downstream steps with the mixed samples. The automation scripts may be fine-tuned in each unit of the machine, and validated with wet runs in its full handling capacity.

DETAILED DESCRIPTION

In general, a high throughput strategy for detecting a pathogen (e.g., viral) mRNA, including in particular, a COVID-19 pathogen, may be configured as a template switching method, which may be used to label the short cDNA fragments at 3' end when the RNA of SARS-CoV-2 is reverse transcribed into cDNA. For example, 96 samples of cDNA may be barcoded individually in a 96-well plate, and then pooled and purified. The purified cDNA mix may be loaded into one well of a second 96-well plate, resulting in each well containing a mix of 96 barcoded cDNA samples. SARS-CoV-2 targets are amplified by multiplex PCR with a panel of 171 pairs of primers that are evenly distributed across the genome of the virus. Each well is labeled with one specific pair of sequencing indexes. The libraries made in the second 96-well plate are pooled, purified and sequenced, e.g., in an Illumina NovaSeq. By sorting the indexes and barcodes, each sample is identified after sequencing. This is illustrated schematically in FIG. 1.

In FIG. 1, the method includes first 101 labeling a plurality (of n samples, e.g., 96) of cDNA samples with barcodes individually during reverse transcription, then pooling all of the plurality of samples, e.g., into a single well (or in duplicates of the pool) 103. Thus, each well of the second plate includes the plurality of cDNA samples. Multiplex PCR may then be performed with the panel of primers to the target pathogen. For example the target pathogen may be SARS-CoV-2. Each of the wells in the second sample (of m pools, e.g., 96 pools) may be labeled with the sequencing indexes to one of the pathogen markers in the panel. Thereafter, all of the samples may be sequenced, 105, and sorted by indexes and then by barcodes.

In the specific example of COVID-19 (e.g., SARS-CoV-2), the method may be referred to as a "CleanPlex" SARS-CoV-2 panel for highly sensitive detection and full-genome interrogation of SARS-CoV-2 by using multiplexed PCR amplification of the viral genome followed by NGS of the PCR products. As demonstrated herein, this SARS-CoV-2 panel has a high sensitivity when used to amplify the full SARS-CoV-2 genome and to detect mutations from a cohort of 13 COVID-19 positive patients with viral loads ranging from 8 to 675,885 copies.

The methods and compositions described herein may allow the detection of mutations caused by fused genes at the RNA level in human pathologies. This method may include a "template switching" step that introduces a barcode onto cDNA concurrently to the RNA being reversely transcribed, as shown in FIG. 2. The method of template switching by increasing its efficiency has been optimized as described herein, and its performance confirmed through extensive verification and validation in sequencing, as shown in FIG. 3. In some variations the method may simultaneously deplete human ribosomal RNA during the reverse transcription-template switching. The method of template switching may be used to barcode cDNA made from SARS-CoV-2 RNA isolates.

For template switching, the intact RNA molecules may be first broken up into 200 bp fragments by incubation at 94° C. for 2-5 minutes in a Magnesium solution, followed by stopping the reaction with EDTA and purification. The fragmentation is mandatory, otherwise only the 5' end of the intact RNA is barcoded. This requires that the SARS-CoV-2 RNA purification method described herein includes a fragmentation step, preferentially before the final purification step.

Viral RNA fragmentation at an early stage of the workflow also provides a safety measure to the operators. Additionally, the cDNA fragments generated by the methods described herein may be beneficial for maintaining the excellent limits of detection (LOD) offered by the multiplex PCR approach. After pooling 96 cDNA samples into a mix, only a fraction is used in the downstream multiplex PCR. The methods and compositions described herein may be successfully used to amplify up to 1 µg (or more) of cDNA in a multiplex PCR reaction. The estimated dilution effect of pooling 96 samples could result in ~5-fold reduction of the number of templates that are available for amplification. The fragmentation randomly breaks one full length RNA of SARS-CoV-2 into ~150 fragments. After dilution of the pooling, about 30 fragments may be funneled into multiplex PCR. In contrast, an intact SARS-CoV-2 RNA could be lost in the dilution.

A panel of 171 pairs of primers (pool 2 of CleanPlex SARS-CoV-2 panel, see, e.g., FIG. 5) was used to amplify the cDNA fragments. The average amplicon insert length in this example was 99 bp. These amplicons span the entire SARS-CoV-2 genome with an average 76 bp gap (76±10 bp) between adjacent amplicons and cover 56.4% of the viral genome. We demonstrated that this panel could be used to detect 1.15 copies of SARS-CoV-2 in a mathematical model, and used 28 amplicons to detect 1.4 copies of the virus. Based on the mathematical model, we estimated that with ~30 fragments of SARS-CoV-2 RNA per sample, the 171-amplicon panel (pool 2) could detect 2 copies of the virus with 95% of confidence.

Since only n (e.g., 96, for a 96 well plate) barcodes are needed for labeling cDNA, these barcodes can be formed by using 4(256 combinations), 5(1024 combinations) or 6 bases (4096 combinations). 96 barcodes will be selected from the above barcode groups to ensure the least interference with the target-specific primers in the downstream multiplex PCR, and ensure the bioinformatic identification during the analysis of the sequencing data.

Empirically, about 80% of the capacity of an Illumina NovaSeq flow cell may be used in sequencing in order to ensure a successful sequencing run. This translates to 35,000 samples in an S2 flow cell, with each lane containing 17,500 samples. Two sets of indexes, each containing 96 indexes, may be used to label the library mixes in a total of four 96-well plates. Even for sequencing in an S4 flow cell, only three sets of indexes are required (FIG. 5). Since the numbers of required indexes are significantly reduced, unique dual indexes (UDI) shall be used to label the library mixes, in order to mitigate the known issue of index hopping when using an Illumina NovaSeq sequencer. In the meantime, the burden of production, QC and management of a large number of indexes is alleviated.

In some variations, the barcodes and indexes are synthesized and plated in a 96-format using 96-well plates, so that they can be easily transferred in application by using a 96-channel pipette in the automatic liquid handler (FIG. 6). The plated barcodes and indexes may be pre-verified for cross-contamination and functionality, and any errors may be corrected before releasing. These procedures may be completed through collaboration with oligo providers, e.g., IDT.

Volume Reduction of the Pooled Mix of cDNA and Libraries

Reverse transcription may be carried out in a 20 µl reaction. Assuming ¼ of the volume of each reaction is used in the next step (the remaining may be archived and/or run in parallel/duplicate), pooling of 7,000 samples would result in 35 ml of cDNA mix. For 14,000 and 35,000 samples, 2 bottles of 35 ml and two bottles of 87 ml of cDNA mixes would be obtained, respectively. In the extreme case of 85,000 samples, 4 bottles of 106 ml of cDNA mixes would be obtained. Experimental testing may be used to find a method of volume reduction that produces the highest quality of purified cDNA mix, while remaining as efficient and cost-effective as possible. Micrograms of cDNA mixes may be used. Optimization may also be used to increase the amplification capacity of the multiplex PCR approach in order to ensure that it amplifies the highest amount (in micrograms) of cDNA mix, while producing the least amount of non-specific amplification products and human rRNA, as well as to ensure that the specific targets to be amplified may display high uniformity and coverage, and may be sequenced on NovaSeq.

After the indexing PCR, the finished libraries may be pooled together, purified, quantified and subjected to sequencing. The pooled volume may be 4~10 ml. The same volume reduction method described above may be used.

Automation

The workflow described herein in also highly compatible with automation, and may be automated. For example, the workflow of the one pool SARS-CoV-2 panel may be further simplified and may become even more user-friendly and fast with automation. Examples of steps in the workflow that may use automatic liquid handling are shown in FIG. 7.

The methods described herein have been successfully scripted using, e.g., a Tecan Evo 150, for the entire workflow described herein, and the Tecan automation process has been validated. These scripts may be helpful for scripting automated liquid handling systems generally. Scripts for RNA purification, cDNA barcoding, pooling and purification may be coded for a liquid handler, e.g. a Hamilton Microlab Star, that handles 384 samples precisely and prevents cross-contamination among the samples.

In some variations manual handling may be used for the loading and unloading of the reactions of cDNA synthesis, multiplex PCR and indexing PCR. The pooling of barcoded cDNA simplifies the downstream operations, and shifts the bottleneck to the steps of RNA purification and cDNA synthesis. A farm of thermal cyclers, each with 384 wells, may be used for reverse transcription. The reaction may be assembled with the help of a liquid handler with a 384-head that operates in 1~20 μl range. After the reaction, the same liquid handler may pick 96 samples from the 384-well plates and pools them together. The number of 96-well plates used for downstream PCR reactions may be reduced to 1~10 plates. For 1~2 plates, the samples could be handled with a 96-channel pipettor for simplicity and speed. The cost per reaction from barcoding cDNA to a finished library may therefore be dramatically reduced (even excluding the costs of viral RNA purification, plastics and sequencing).

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A high throughput method of diagnosing RNA of a pathogen by using a multiplex primer extension reaction, the method comprising:
   purifying pathogen RNA from a plurality of clinical specimens;
   breaking the RNA into fragments;
   converting RNA into n cDNA preparations by reverse transcription, in one or more multi-well plates, and labeling each cDNA preparation with a barcode by a template switching reaction that takes place simultaneously;
   wherein the cDNA is synthesized during the conversion of the RNA into n cDNA preparations by using an oligo (dT), a hexamer primer, a template switching oligo and a reverse transcriptase;
   pooling each of the n cDNA preparations into one vessel, purifying the cDNA, and loading the purified cDNA mix into a plurality of m wells of one or more new multi-well plates;
   amplifying a plurality of targets of the pathogen in each of the m wells by multiplex PCR with a plurality of target-specific primers to form m libraries, followed by indexing PCR where each of the m wells is labeled with one specific pair of sequencing indexes;
   mixing all of the m libraries made in the m multi-well plates into one or more pools, purifying and sequencing the one or more pools in a next generation sequencer; and
   sorting the indexes and barcodes to identify each sample.

2. The method of claim 1, wherein the pathogen RNA is total RNA, mRNA, fragmented total RNA, or fragmented mRNA purified from one or more of: nasopharyngeal swabs, blood, plasma, body fluid, feces, Formalin-fixed, and Paraffin-embedded (FFPE) tissue samples (FFPE RNA).

3. The method of claim 1, wherein the pathogen RNA is total RNA containing RNA of SARS-CoV-2 virus purified from one or more of: nasopharyngeal swabs, blood, plasma, body fluid, feces, Formalin-fixed, and Paraffin-embedded (FFPE) tissue samples (FFPE RNA).

4. The method of claim 1, wherein the plurality of target-specific primers includes a target-specific region that is complimentary to a plurality of target RNA.

5. The method of claim 1, wherein the plurality of target-specific primers includes a target-specific region that is complimentary to a plurality of target RNA.

6. A high throughput method of diagnosing SARS-CoV-2 using a multiplex primer extension reaction, the method comprising:
   purifying RNA including SARS-CoV-2 RNA from a plurality of clinical specimens;
   breaking the RNA into fragments;
   converting RNA into n cDNA preparations by reverse transcription, in one or more multi-well plates, and labeling each cDNA preparation with a barcode by a template switching reaction that takes place simultaneously;
   wherein the cDNA is synthesized during the conversion of the RNA into n cDNA preparations by using an oligo (dT), a hexamer primer, a template switching oligo and a reverse transcriptase;
   pooling each of the n cDNA preparations into one vessel to form a cDNA mix, purifying the cDNA, and loading the purified cDNA mix into a plurality of m wells of one or more new multi-well plates;
   amplifying a plurality of targets of the SARS-CoV-2 in each of the m wells by multiplex PCR with a plurality of SARS-CoV-2 specific primers to form m libraries, followed by indexing PCR where each of the m wells is labeled with one specific pair of sequencing indexes;
   mixing all of the m libraries made in the m multi-well plates into one or more pools, purifying and sequencing the one or more pools in a next generation sequencer; and
   sorting the indexes and barcodes to identify each sample.

7. The method of claim 6, wherein the plurality of SARS-CoV-2 specific primers form amplicons that span greater than 50% of a genome of SARS-Cov-2.

8. The method of claim 6, wherein the plurality of SARS-CoV-2 specific primers form amplicons that span greater than 80% of a genome of SARS-Cov-2.

9. The method of claim 6, wherein the template switching reaction comprises a template switching oligo.

10. The method of claim 9, wherein the template switching oligo contains a barcode or a unique molecular index comprising 3-8 random nucleotides.

11. The method of claim 6, wherein the cDNA is synthesized during the conversion of the RNA into n cDNA preparations by using 0.2-2 uM of oligo(dT), 1-10 uM of hexamer primer, 1-10 uM of template switching oligo and 10-200 units of reverse transcriptase at 42° C. for 90 minutes.

12. The method of claim 6, wherein the reverse transcription reaction is further treated by using an exonuclease, multiple exonucleases, or a combination of exonucleases and nucleases, selected from the group comprising: S1 nuclease, P1 nuclease, mung bean nuclease, lambda exonuclease, exonuclease I, exonuclease VII, exonuclease T, RecJ, RecJf.

13. The method of claim 6, wherein the plurality of SARS-CoV-2 specific primers comprises either forward primers or reverse primers.

14. The method of claim 6, wherein the plurality of SARS-CoV-2 specific primers comprises both forward primers and reverse primers.

15. The method of claim 6, wherein each primer of the plurality of SARS-CoV-2 specific primers includes a SARS-CoV-2 specific region that is from 8-50 nucleotides.

16. The method of claim 6, wherein said plurality of SARS-CoV-2 specific primers comprise between 7 SARS-CoV-2 specific primers and 1,000,000 SARS-CoV-2 specific primers.

17. The method of claim 6, wherein each primer of the plurality of SARS-CoV-2 specific primers includes a SARS-CoV-2 specific region comprising unmodified oligonucleotides.

18. The method of claim 6, wherein each primer of the plurality of SARS-CoV-2 specific primers includes a SARS-CoV-2 specific region comprising modified oligonucleotides with chemical modifications of nucleotides.

19. The method of claim 6, wherein each primer of the plurality of SARS-CoV-2 specific primers comprises a region of nucleotide sequence used for further amplification and for high-throughput sequencing.

20. The method of claim 6, comprising further purifying the cDNA using magnetic beads or a DNA purification column.

21. The method of claim 6, wherein the multiplex primer extension reaction is a multiplex polymerase chain reaction.

22. The method of claim 6, wherein the multiplex primer extension reaction is further treated by using an exonuclease, multiple exonucleases, or a combination of exonucleases and nucleases, selected from the group comprising: S1 nuclease, P1 nuclease, mung bean nuclease, lambda exonuclease, exonuclease I, exonuclease VII, exonuclease T, RecJ, RecJf.

23. The method of claim 21, further comprising amplifying the products of the multiplex polymerase chain reaction with a pair of primers that contain sequencing indexes, or unique dual indexes.

24. The method of claim 6, further comprising analyzing the amplification products by high-throughput sequencing.

* * * * *